(12) United States Patent
Barak et al.

(10) Patent No.: US 7,455,982 B2
(45) Date of Patent: *Nov. 25, 2008

(54) AUTOMATED METHODS OF DETECTING RECEPTOR ACTIVITY

(75) Inventors: Larry S. Barak, Durham, NC (US); Robert H. Oakley, Durham, NC (US)

(73) Assignee: Molecular Devices Corporation, Sunnyvale, CA (US)

( * ) Notice: Subject to any disclaimer, the term of this patent is extended or adjusted under 35 U.S.C. 154(b) by 262 days.

This patent is subject to a terminal disclaimer.

(21) Appl. No.: 11/084,928

(22) Filed: Mar. 21, 2005

(65) Prior Publication Data

US 2005/0181423 A1 Aug. 18, 2005

Related U.S. Application Data

(60) Continuation of application No. 10/629,176, filed on Jul. 29, 2003, now abandoned, which is a division of application No. 10/095,620, filed on Mar. 12, 2002, now abandoned.

(60) Provisional application No. 60/275,339, filed on Mar. 13, 2001.

(51) Int. Cl.
*G01N 33/53* (2006.01)
*C12Q 1/00* (2006.01)
*C12N 5/00* (2006.01)
*C07K 1/00* (2006.01)

(52) U.S. Cl. ............................ 435/7.2; 435/4; 435/7.1; 435/325; 530/350

(58) Field of Classification Search ....................... None
See application file for complete search history.

(56) References Cited

U.S. PATENT DOCUMENTS

| | | | |
|---|---|---|---|
| 4,219,335 A | 8/1980 | Ebersole | |
| 4,324,633 A | 4/1982 | Lovejoy | |
| 4,908,773 A | 3/1990 | Pantoliano et al. | |
| 5,324,633 A | 6/1994 | Fodor et al. | |
| 5,521,705 A * | 5/1996 | Oldenbourg et al. | 356/368 |
| 5,548,661 A * | 8/1996 | Price et al. | 382/133 |
| 5,574,656 A | 11/1996 | Agrafiotis et al. | |
| 5,670,113 A | 9/1997 | Akong et al. | |
| 5,684,711 A | 11/1997 | Agrafiotis et al. | |
| 5,705,335 A | 1/1998 | Hendry | |
| 5,770,176 A | 6/1998 | Nargessi | |
| 5,854,004 A | 12/1998 | Czernilofsky et al. | |
| 5,864,488 A | 1/1999 | Isaacs et al. | |
| 5,874,219 A | 2/1999 | Rava et al. | |
| 5,891,646 A | 4/1999 | Barak et al. | |
| 5,912,122 A | 6/1999 | Daggett et al. | |
| 5,919,646 A | 7/1999 | Okun et al. | |
| 5,972,629 A | 10/1999 | Niman | |
| 5,972,639 A | 10/1999 | Parandoosh | |
| 5,987,390 A | 11/1999 | Ladunga | |
| 5,989,835 A * | 11/1999 | Dunlay et al. | 435/7.2 |
| 6,017,496 A | 1/2000 | Nova et al. | |
| 6,025,129 A | 2/2000 | Nova et al. | |
| 6,027,890 A | 2/2000 | Ness et al. | |
| 6,057,114 A | 5/2000 | Akong et al. | |
| 6,100,026 A | 8/2000 | Nova et al. | |
| 6,110,693 A | 8/2000 | Barak et al. | |
| 6,124,102 A | 9/2000 | Fodor et al. | |
| 6,127,133 A | 10/2000 | Akong et al. | |
| 6,199,017 B1 | 3/2001 | Tomonaga et al. | |
| 6,203,987 B1 | 3/2001 | Friend et al. | |
| 6,219,622 B1 | 4/2001 | Schmidt | |
| 6,221,600 B1 | 4/2001 | MacLeod et al. | |
| 6,221,612 B1 | 4/2001 | Knapp et al. | |

FOREIGN PATENT DOCUMENTS

WO    WO 00/03246    1/2000

OTHER PUBLICATIONS

Vrecl et al., Molecular Endocrinology 12: 1818-1829, 1998.*
Eric Weisstein's world of Mathematics, 1-3.*
Barak, Larry S.,"A β-Arrestin/Green Fluorescent Protein Biosensor for Detecting G Protein-coupled Receptor Activation",*Journal of Biological Chemistry*, vol. 44, No. 272, pp. 27497-27500 (Oct. 31, 1997).

(Continued)

*Primary Examiner*—Robert Landsman
*Assistant Examiner*—Gyan Chandra
(74) *Attorney, Agent, or Firm*—Gargi Talukder; David J. Brezner; Morgan Lewis & Bockius LLP

(57) ABSTRACT

Methods of detecting G protein-coupled receptor (GPCR) activity in vitro and in vivo are provided. In one embodiment, the method includes providing at least one cell that expresses a GPCR and a plurality of conjugated proteins. Each of the plurality of conjugated proteins is formed by conjugating an arrestin protein and a detectable molecule. The plurality of conjugated proteins are substantially evenly distributed in the cytoplasm of the at least one cell. A first image of the at least one cell is obtained by detecting an amount of energy emitted from the detectable molecules and storing a value relative to the amount of energy. The at least one cell is treated with an agonist. A second image of the at least one cell is obtained. The first image and the second image are compared to detect the localization of at least some of the plurality of conjugated proteins at endocytic vesicles and/or endosomes.

6 Claims, 5 Drawing Sheets

OTHER PUBLICATIONS

Barak, Larry S.,"Internal Trafficking and Surface Mobility of a Functionally Intact B2-Adrenergic Receptor-Green Fluorescent Protein Conjugate",*Molecular Pharmacology*, vol. 51, No. 2, pp. 177-184 (Feb. 1997),177-184.

Barak, Larry S.,et al.,"Real-time Visualization of the Cellular Redistribution of G Protein-coupled Receptor Kinase 2 and β-Arrestin 2 during Homologous Desensitization of the Substance P Receptor",*The Journal of Biological Chemistry*, vol. 274, No. 11, pp. 7565-7569 (Mar. 12, 1999),7565-7569.

Zhang, Jie ,et al.,"Cellular Trafficking of G Protein-coupled Receptor/β-Arrestin Endocytic Complexes",*The Journal of Biological Chemistry*, vol. 274, No. 16, pp. 10999-11006 (Apr. 16, 1999),10999-11006.

Robert H. Oakley, et al., "Differential Affinities of Visual Arrestin, βArrestin1, and βArrestin2 for G Protein-coupled Receptors Delineate Two Major Classes of Receptors", The Journal of Biological Chemistry, Jun. 2, 2000; pp. 17201-17210, USA.

Stéphane A. Laporte, et al., "The Interaction of βArrestin with the AP-2 Adaptor is Required for the Clustering of $β_2$-Adrenergic Receptor into Clathrin-coated Pits", The Journal of Biological Chemistry, Jul. 28, 2000; pp. 23120-23126, USA.

Robert H. Oakley, et al., "Association of βArrestin with G Protein-coupled Receptors during Clathrin-mediated Endocytosis Dictates the Profile of Receptor Resensitization", The Journal of Biological Chemistry, Nov. 5, 1999; pp. 32248-32257, USA.

Han Htun, et al., "Visualization of glucocorticoid Receptor Translocation and Intranuclear Organization in Living Cells with an Green Fluorescent Protein Chimera", Proc. Nat'l. Acad. Sci., May 1996, vol. 93, pp. 4845-4850, USA.

Kimberly L. Carey, et al., "Evidence Using a Green Fluorescent Protein-Glucocorticoid Receptor Chimera that the RAN/TC4 and GTPase Mediates an Essential Function Independent of Nuclear Protein Import", The Rockefeller University Press, XP 000670316, 1996, USA.

* cited by examiner

FIG. 3A
FIG. 3B
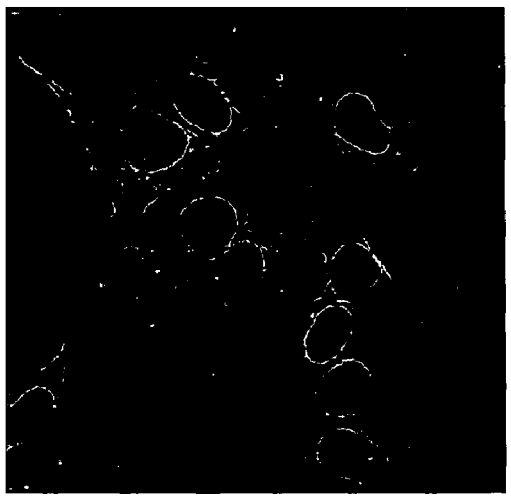
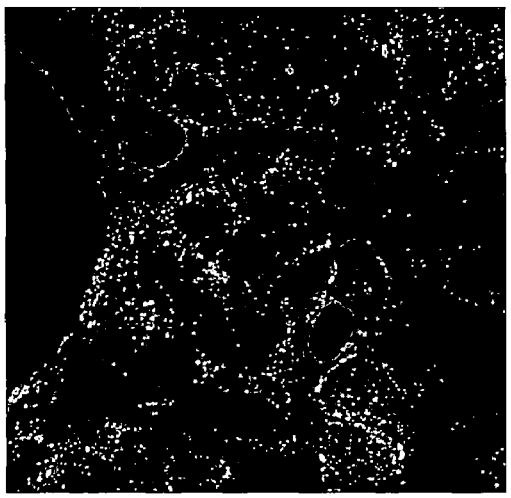
FIG. 4A
FIG. 4B

AUTOMATED METHODS OF DETECTING RECEPTOR ACTIVITY

CROSS-REFERENCE TO RELATED APPLICATION

This application is a continuation of U.S. application Ser. No. 10/629,176, filed Jul. 29, 2003 now abandoned, which is a divisional of U.S. application Ser. No. 10/095,620, filed on Mar. 12, 2002, which claims the benefit of U.S. Provisional Application No. 60/275,339, filed Mar. 13, 2001; the entire disclosures of these applications are hereby incorporated herein by reference.

STATEMENT REGARDING FEDERALLY-SPONSORED RESEARCH OR DEVELOPMENT

This work was supported by the U.S. Government under Grant No. HL61365 awarded by the National Institutes of Health. The U.S. Government may have certain rights in the invention.

BACKGROUND

The present invention relates to methods of detecting G protein-coupled receptor (GPCR) activity in vitro and in vivo. The present invention provides methods for identifying compounds that activate the GPCR regulatory pathway and methods for identifying ligands of GPCRs.

G protein-coupled receptors (GPCRs) are cell surface proteins that translate hormone or ligand binding into intracellular signals. GPCRs are found in all animals, insects, and plants. GPCR signaling plays a pivotal role in regulating various physiological functions including phototransduction, olfaction, neurotransmission, vascular tone, cardiac output, digestion, pain, and fluid and electrolyte balance. Although they are involved in various physiological functions, GPCRs share a number of common structural features. They contain seven membrane domains bridged by alternating intracellular and extracellular loops and an intracellular carboxyl-terminal tail of variable length.

The magnitude of the physiological responses controlled by GPCRs is linked to the balance between GPCR signaling and signal termination. The signaling of GPCRs is controlled by a family of intracellular proteins called arresting. Arrestins bind activated GPCRs, including those that have been agonist-activated and especially those that have been phosphorylated by G protein-coupled receptor kinases (GRKs).

Receptors, including GPCRs, have historically been targets for drug discovery and therapeutic agents because they bind ligands, hormones, and drugs with high specificity. Approximately fifty percent of the therapeutic drugs in use today target or interact directly with GPCRs. See eg., Jurgen Drews, (2000) "Drug Discovery: A Historical Perspective," *Science* 287:1960-1964.

Although only several hundred human GPCRs are known, it is estimated that several thousand GPCRs exist in the human genome. Of these known GPCRs, many are orphan receptors that have yet to be associated with a function or ligands.

One method of assaying GPCR activity, as disclosed in U.S. Pat. Nos. 5,891,646, and 6,110,693, both to Barak et al., uses a cell expressing a GPCR and a conjugate of an arrestin and a detectable molecule.

Accordingly, there is a need to provide accurate, easy to interpret methods of detecting G protein-coupled receptor activity.

SUMMARY

In accordance with one aspect of the present invention, a method of detecting G protein-coupled receptor (GPCR) pathway activity is provided. The method includes providing at least one cell that expresses a GPCR and a plurality of conjugated proteins. Each of the plurality of conjugated proteins is formed by conjugating an arrestin protein and a detectable molecule. The plurality of conjugated proteins are substantially evenly distributed in the cytoplasm of the at least one cell. A first image of the at least one cell is obtained by detecting an amount of energy emitted from the detectable molecules and storing a value relative to the amount of energy. The at least one cell is treated with a test compound. A second image of the at least one cell is obtained. The first image and the second image are compared to detect the localization of at least some of the plurality of conjugated proteins. The localization may occur at endocytic vesicles and/or endosomes.

In accordance with another aspect of the invention, a method of detecting G protein-coupled receptor (GPCR) pathway activity is provided whereby at least one cell that expresses a GPCR and a plurality of conjugated proteins are provided. Each of the plurality of conjugated proteins is formed by conjugating an arrestin protein and a detectable molecule. The plurality of conjugated proteins are substantially evenly distributed in the cytoplasm of the at least one cell. A first digital image of the at least one cell is obtained by detecting and measuring energy emitted from the detectable molecules. The first digital image is formed from an array of a plurality of pixels each having respective intensity values. A respective intensity value is based on the intensity of energy emitted from the detectable molecules associated with a pixel's location in the array. The at least one cell is treated with a test compound. A second digital image of the at least one cell is obtained by detecting and measuring energy emitted from the detectable molecules. The second digital image is formed from an array of a plurality of pixels each having respective intensity values. A respective intensity value is based on the intensity of energy emitted from the detectable molecules associated with a pixel's location in the array. The first digital image and the second digital image are compared to detect the localization of at least some of the plurality of conjugated proteins. The localization may occur at endocytic vesicles and/or endosomes. The localization of at least some of the plurality of conjugated proteins are detected by a change in apparent intensity of energy emitted from detectable molecules resulting in an increase in the value of at least some of the plurality of pixels.

In accordance with yet another aspect of the invention, a method of detecting G protein-coupled receptor (GPCR) pathway activity is provided. At least one cell that expresses a GPCR and a plurality of conjugated proteins is provided. Each of the plurality of conjugated proteins is formed by conjugating an arrestin protein and a detectable molecule. The plurality of conjugated proteins are substantially evenly distributed in the cytoplasm of the at least one cell. The at least one cell is treated with a test compound. A digital image of the at least one cell is obtained by detecting and measuring energy emitted from the detectable molecules. The digital image is formed from an array of a plurality of pixels each having respective intensity values. A respective intensity value is based on the intensity of energy emitted from the detectable molecules associated with a pixel's location in the array. The localization of at least some of the plurality of conjugated proteins may be detected at endocytic vesicles and/or endosomes. The localization of at least some of the plurality of conjugated proteins is detected by a change in apparent intensity of energy emitted from detectable molecules resulting in a value of at least some of the plurality of pixels above a threshold intensity.

It should be emphasized that the term "comprises" or "comprising," when used in this specification, is taken to specify the presence of stated features, steps, or components, but does not preclude the presence or addition of one or more other features, steps, components, or groups thereof.

BRIEF DESCRIPTION OF DRAWINGS

The objects and advantages of the invention will be understood by reading the following detailed description in conjunction with the drawings in which:

FIGS. 3a and 3b are confocal microscopic images of βarr-GFP fluorescence in cells stably expressing βarr-GFP fusion protein and the V2R (GPCR) of which:

FIG. 3a is before treatment with an agonist (Control) and

FIG. 3b is after a 30 min. treatment with agonist at 37° C.;

FIGS. 4a and 4b are identical to FIGS. 3a and 3b, respectively, except that they were taken at a reduced detector sensitivity to prevent saturation of the detector;

FIGS. 5a and 5b show confocal microscope images taken at reduced intensity with the pixels above the threshold intensity (here calculated as those within the >99th percentile) appearing as lightly shaded regions, of which:

FIG. 5a is of the control group and

FIG. 5b is of the treated cells;

DETAILED DESCRIPTION

Figure 1:
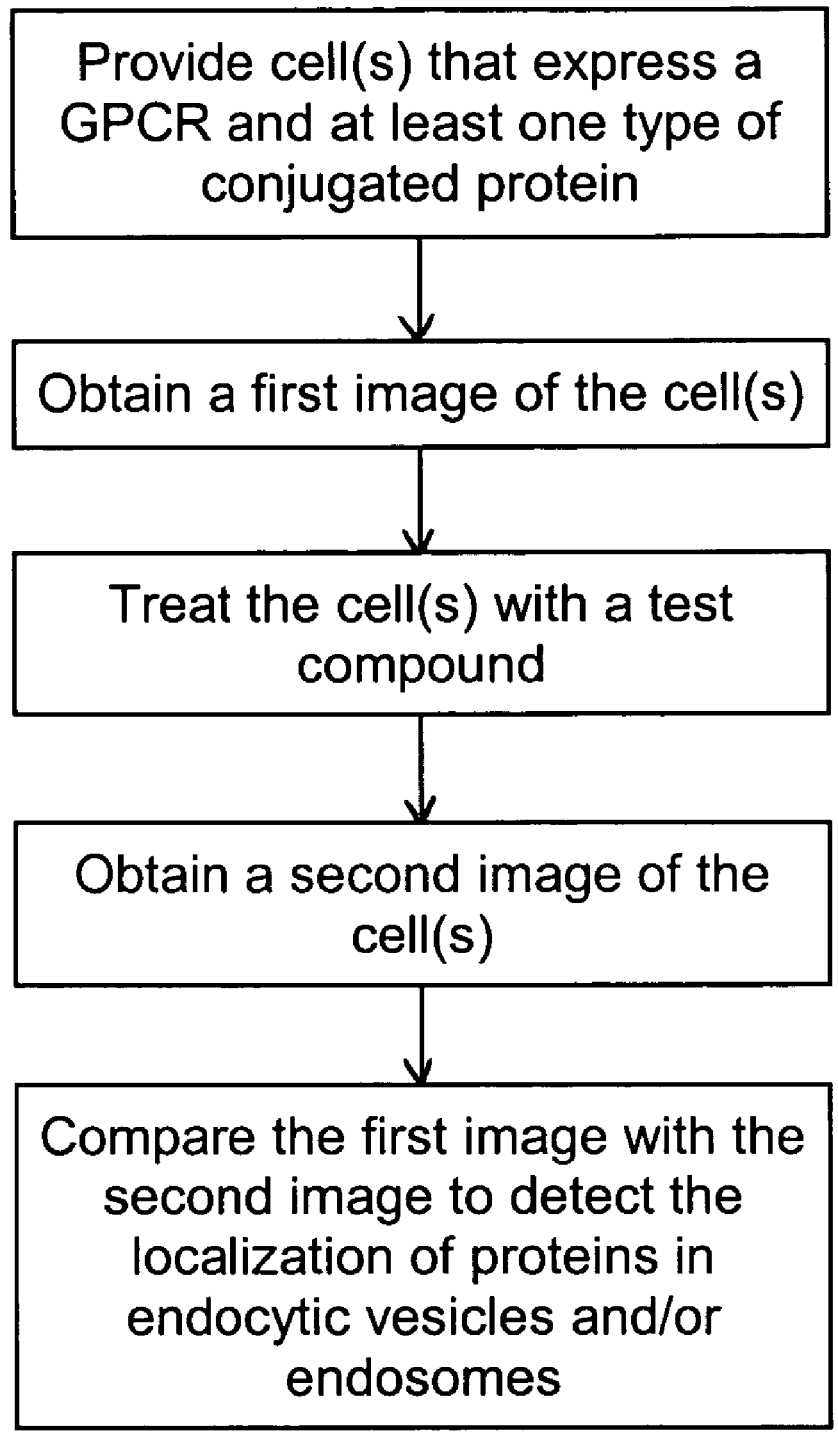
FIG. 1 is a flow diagram of a method of detecting receptor activity in accordance with the invention.

Automated screening methods to detect GPCR pathway activity are provided. The methods may be used to determined whether the level of GPCR pathway has changed. The methods provide convenient, real time, high volume methods of screening compounds and/or solutions for GPCR activity.

The methods offer the advantage of providing a gross comparison of the relative intensities of scans of cells before and after exposure to a test compound for a quick and simple determination of the activity of the test compound. Examples of test compounds include potential ligands, potential agonists, potential antagonists, and potential desensitization agents. The methods do not require qualitative analyzes of an image with respect to location of a detectable molecule and the detectable molecule's proximity to any specific cell structure. The method also does not require determinations of area of specific cell structures or any measurements within the cell nucleus. The methods will facilitate the rapid screening of compounds in an automated process.

Examples of assays with which the methods may be used include, but are not limited to, those as described in U.S. Pat. Nos. 5,891,646 and 6,110,693, and U.S. application Ser. No. 09/993,844, filed Nov. 5, 2001, the disclosures of which are hereby incorporated by reference in their entirety. Additional examples of assays with which the methods may be used include, but are not limited to, assays using Fluorescent Resonance Energy Transfer (FRET) and assays using Bioluminescence Resonance Energy Transfer (BRET) technology as described in Angers, S., Salahpour, A., Joly, E., Hilairet, S., Chelsky, "β2-adrenergic receptor dimerization in living cells using bioluminescence resonance energy transfer (BRET)," Proc. Nat'l. Acad. Sci. USA 97, 7: 3684-3689.

Through a process called desensitization, G protein-coupled receptor kinases (GRKs) phosphorylate intracellular domains of GPCRs, for example, at the carboxyl-terminal tail. The carboxyl-terminal tail of many GPCRs begins shortly after the conserved NPXXY (SEQ ID NO:40) motif that marks the end of the seventh transmembrane domain (i.e. what follows the NPXXY (SEQ ID NO:40) motif is the carboxyl-terminal tail of the GPCR). The carboxyl-terminal tail may be relatively long (approximately tens to hundreds of amino acids), relatively short (approximately tens of amino acids), or virtually non-existent (less than approximately ten amino acids). As used herein, "carboxyl-terminal tail" shall mean all three variants (whether relatively long, relatively short, or virtually non-existent).

After phosphorylation, an arrestin protein associates with the GRK-phosphorylated receptor and uncouples the receptor from its cognate G protein. It will be understood that the term "arrestin" refers to all types of naturally occurring and engineered variants of arrestin, including, but not limited to, visual arrestin (sometimes referred to as Arrestin 1), β-arrestin 1 (sometimes referred to as Arrestin 2), and β-arrestin 2 (sometimes referred to as Arrestin 3). The interaction of the arrestin with the phosphorylated GPCR terminates GPCR signaling and produces a non-signaling, desensitized receptor.

The arrestin bound to the desensitized GPCR targets the GPCR to clathrin-coated pits for endocytosis. The stability of the interaction of arrestin with the GPCR may dictate the rate of GPCR dephosphorylation, recycling, and resensitization. When the GPCR has an enhanced affinity for arrestin, the GPCR/arrestin complex remains intact and is internalized into endosomes.

To monitor GPCR activity, an in vivo or in vitro environment may be utilized. In both environments, a conjugate of an arrestin protein and a detectable molecule is utilized. The term "detectable molecule" means any molecule capable of detection by spectroscopic, photochemical, biochemical, immunochemical, electrical, radioactive, and optical means, including but not limited to, fluorescence, phosphorescence, and bioluminescence and radioactive decay. Detectable molecules include, but are not limited to, GFP, luciferase, β-galactosidase, rhodamine-conjugated antibody, and the like. Detectable molecules include radioisotopes, epitope tags, affinity labels, enzymes, fluorescent groups, chemiluminescent groups, and the like. Detectable molecules include molecules which are directly or indirectly detected as a function of their interaction with other molecule(s).

GFP includes various naturally occurring forms of GFP that may be isolated from natural sources or genetically engineered, as well as artificially modified GFPs. GFPs are well known in the art. See, for example, U.S. Pat. Nos. 5,625,048; 5,777,079; and 6,066,476. It is well understood in the art that GFP is readily interchangeable with other fluorescent proteins, isolated from natural sources or genetically engineered, including, but not limited to, yellow fluorescent proteins (YFP), red fluorescent proteins (RFP), cyan fluorescent proteins (CFP), UV excitable fluorescent proteins, or any wavelength in between.

The methods are designed to detect changes in the location of the conjugate of an arrestin protein and a detectable molecule after exposure of the cells to test compounds, test solutions, and test conditions.

In an in vivo environment, one or more cells that express a GPCR and that contain a conjugate of an arrestin protein and a detectable molecule are provided. Arrestin coupled to a detectable molecule may be detected and monitored. The location of the arrestin may be detected, for example, evenly distributed in the cell cytoplasm, concentrated at a cell membrane, and/or localized in endocytic vesicles. In response to agonist stimulation, the proximity of arrestin to a GPCR may be monitored, as well as the proximity to any other cell structure. For example, in response to agonist stimulation arrestin may be detected in proximity to GPCRs at a cell membrane and/or colocalized with a GPCR in endocytic vesicles.

In an in vitro environment, a substrate having deposited thereon one or more GPCRs having arrestin binding sites and agonist binding sites is provided, and a buffered solution comprising one or more conjugates of an arrestin protein and a detectable molecule is provided. The GPCR can be positioned on the substrate such that the arrestin binding sites are exposed to the arrestin and the agonist binding sites are accessible to agonists. The GPCR and arrestin may be obtained from whole cells and used in the in vitro assay after purification. The GPCR has arrestin binding sites and agonist binding sites and may be supported in a multilayer or bilayer lipid vesicle. The vesicle supporting the GPCR is deposited on the substrate, and the GPCR is supported in the lipid vesicle and deposited on the substrate such that the arrestin binding sites are exposed to arrestin and the receptor binding sites are accessible to agonists. The substrate may be any artificial substrate on which the modified GPCR may be deposited, including but not limited to, glass, plastic, diamond, ceramic, semiconductor, silica, fiber optic, biocompatible monomer, biocompatible polymer, polymer beads (including organic and inorganic polymers), and the like.

The location of the arrestin may be detected and monitored in the in vitro environment. In response to agonist stimulation, the redistribution of arrestin may be detected. For example, in response to agonist stimulation, arrestin may be detected in proximity to GPCRs on the substrate, arrestin may be detected to compartmentalize, and the like.

GPCRs

The method may be utilized with any membrane receptor protein in which agonist binding is linked to association of arrestin proteins. An illustrative, non-limiting list of known GPCRs with which the present invention may be used is contained in Table 1. The receptors are grouped according to classical divisions based on structural similarities and ligands. GPCRs that may be used in the present invention include known GPCRs, unknown or orphan GPCRs, and chimeric or modified GPCRs. A GPCR is considered to be an "unknown or orphan GPCR" if its function and/or ligands are unknown. Modified GPCRs include GPCRs that have one or more modifications in the carboxyl-terminal tail, modifications in the intracellular loop(s), and/or in the cytoplasmic end of the transmembrane region, preferably in the carboxyl-terminal tail.

By way of example, three major classes of GPCRs for known receptors have been identified: Class A receptors, Class B receptors, and receptors with virtually non-existent carboxyl-terminal tails. The receptors are classified accordingly based on their interactions with and affinity for rat β-arrestin-2 in HEK-293 cells and may be predicted based on the amino acid residues in their carboxyl-terminal tail and the length of their carboxyl-terminal tail. A Class B receptor is a GPCR that has one or more sites of phosphorylation, preferably clusters of phosphorylation sites, properly positioned in its carboxyl-terminal tail such that it does recruit rat β-arrestin-2 to endosomes in HEK-293 cells under conditions as described in U.S. Pat. No 5,891,646 and Oakley, et al. "Differential Affinities of Visual Arrestin, βArrestin1, and βArrestin2 for G Protein-coupled Receptors Delineate Two Major Classes of Receptors," Journal of Biological Chemistry, Vol 275, No. 22, pp 17201-17210, Jun. 2, 2000, the contents of which are hereby incorporated by reference in their entirety. A Class A receptor is a GPCR that does not have one or more sites of phosphorylation, preferably clusters of phosphorylation sites, properly positioned in its carboxyl-terminal tail such that it does not recruit rat β-arrestin-2 to endosomes in HEK-293 cells under conditions as described above for Class B receptors. Receptors with virtually non-existent carboxyl-terminal tails include, for example, olfactory and taste receptors.

Table 2 is an illustrative, non-limiting list of known receptors, including the amino acid sequence for their carboxyl terminal tails and appropriate classification. For the Class B receptor examples, the residues that may function as clusters of phosphorylation sites are shown in bolded italics.

In the present invention, modified GPCRs are preferred. The modified GPCRs include GPCRs that have been modified to have one or more sites of phosphorylation, preferably clusters of phosphorylation sites, properly positioned in its carboxyl-terminal tail. These clusters of phosphorylation sites are preferably serine and threonine residues located in the carboxyl-terminal tail of the GPCR. These clusters are remarkably conserved in their position within the carboxyl-terminal tail domain and serve as primary sites of agonist-dependent phosphorylation. The clusters of amino acids may occupy two out of two, two out of three, three out of three, three out of four, four out of four, four out of five, five out of five, and the like consecutive amino acid positions. Accordingly, the clusters of amino acids that promote formation of a stable GPCR/arrestin complex are "clusters of phosphorylation sites."

The modified GPCRs containing one or more sites of phosphorylation, preferably clusters of phosphorylation sites, properly positioned in its carboxyl-terminal tail have an increased affinity for arrestin and colocalize with arrestin in endosomes after stimulation with agonist. These modified GPCRs recruit arrestin to endosomes within approximately 30 minutes of agonist stimulation. The one or more sites of phosphorylation, preferably clusters of phosphorylation sites, must be optimally positioned within the GPCR tail for the GPCR to have an increased affinity for arrestin.

The modified GPCRs may be constructed such that the one or more sites of phosphorylation, preferably clusters of phosphorylation sites, are optimally positioned within the carboxyl-terminal tail. The portions of polypeptides, which are to be fused together to form the modified GPCR, are chosen such that the one or more sites of phosphorylation, preferably clusters of phosphorylation sites, are reliably positioned properly within the carboxyl-terminal tail. In the alternative, the location of discrete point mutations to create the modified GPCR may be chosen so that the one or more sites of phosphorylation, preferably clusters of phosphorylation sites, are properly positioned within the carboxyl-terminal tail.

Cells

Cells useful in the present invention include eukaryotic and prokaryotic cells, including, but not limited to, bacterial cells, yeast cells, fungal cells, insect cells, nematode cells, plant cells, and animal cells. Suitable animal cells include, but are not limited to, HEK cells, HeLa cells, COS cells, U208 cells, and various primary mammalian cells. An animal model expressing a conjugate of an arrestin and a detectable molecule throughout its tissues or within a particular organ or tissue type, may be useful in studying cellular targets of known or unknown GPCR ligands.

Cells useful in the present invention include those that express a known GPCR, a variety of known GPCRs, an unknown GPCRs, a variety of unknown GPCRs, a modified GPCR, a variety of modified GPCRs, and combinations thereof. A cell that expresses a GPCR is one that contains the GPCR as a functional receptor in its cell membrane. The cells may naturally express the GPCRs or may be genetically engineered to express the GPCRs. As one skilled in the art readily would understand, the cells may be genetically engineered to express GPCRs by molecular biological techniques standard in the genetic engineering art.

The Conjugates

In the methods of the present invention, a conjugate of an arrestin protein and a detectable molecule is utilized.

All forms of arrestin, both naturally occurring and engineered variants, including but not limited to, visual arrestin, β-arrestin 1 and β-arrestin 2, may be used in the present invention. The GPCRs of the present invention having enhanced affinity motifs in their carboxyl-terminal tails (naturally-occurring and modified) may interact to a detectable level with all forms of arrestin.

Detectable molecules that may be used to conjugate with the arrestin include, but are not limited to, molecules that are detectable by spectroscopic, photochemical, radioactivity, biochemical, immunochemical, electrical, and optical means, including but not limited to, bioluminescence, phosphorescence, and fluorescence. These detectable molecules should be biologically compatible molecules and should not compromise the ability of the arrestin to interact with the GPCR system, and the interaction of the arrestin with the GPCR system must not compromise the ability of the detectable molecule to be detected. Preferred detectable molecules are optically detectable molecules, including optically detectable proteins, such that they may be excited chemically, mechanically, electrically, or radioactively to emit fluorescence, phosphorescence, or bioluminescence. Optically detectable molecules include, for example, beta-galactosidase, firefly luciferase, bacterial luciferase, fluorescein, Texas Red, and rhodamine-conjugated antibody. More preferred detectable molecules are inherently fluorescent molecules, such as fluorescent proteins, including, for example, Green Fluorescent Protein (GFP).

The detectable molecule may be conjugated to the arrestin protein by methods as described in Barak et al. (U.S. Pat. Nos. 5,891,646 and 6,110,693). The detectable molecule may be conjugated to the arrestin at the front-end, at the back-end, or in the middle. Preferably, the detectable molecules are molecules that are capable of being synthesized in the cell. The cell can be transfected with DNA so that the conjugate of arrestin and a detectable molecule is produced within the cell. As one skilled in the art readily would understand, cells may be genetically engineered to express the conjugate of arrestin and a detectable molecule by molecular biological techniques standard in the genetic engineering art.

Methods of Detection

The methods of detection can be used to determine the distribution and/or location of the detectable molecules conjugated to the arrestin protein. Thus, the methods of detection may vary depending on the detectable molecule or molecules used. The methods of detection may be used to determine the intracellular location of the arrestin protein or interaction of the arrestin protein with a GPCR, for example, the concentration of arrestin at a cell membrane or the colocalization of arrestin protein with GPCR in an endocytic vesicle. One skilled in the art will readily be able to devise detection methods suitable for the detectable molecule or molecules used.

The detectable molecules emit, reflect, and/or absorb energy depending on the detectable molecule used. For the purposes of clarity, the term "emit" is used in this specification, but should be interpreted to include "reflect" and "absorb" unless stated otherwise. The detector and method of detection used should be suitable for recognizing and recording the type of energy emitted. The detector utilized may image the cell point by point in series or in parallel, for example, using a single photodetector or a charge-coupled device array. Such configurations of detectors are known to the art.

The detection methods may include using a detector for measuring the intensity of the energy emitted from the detectable molecules and may be operatively coupled to a computer controller for controlling the operation of the detector and performing an analysis of the signals received. The controller preferably includes a computer program product for performing analysis of the signals received from the detectors. The computer program product may be written specifically for use with the detection method or may be a commercially available program modified for use with the detection method.

For optically detectable molecules, any optical method may be used where fluorescence, bioluminescence, or phosphorescence may be measured and recorded. For example, one or more photodetectors for measuring fluorescence may be used and these photodetectors may be operatively coupled to a computer controller. A charge-coupled device array may also be used and may be operatively coupled to a computer controller.

In a preferred embodiment, arrestin may be conjugated to GFP and the arrestin-GFP conjugate may be viewed by confocal microscopy.

Automated Methods of Detecting GPCR Pathway Activity

FIG. 1 is a flow diagram of a method of detecting receptor activity in accordance with one aspect of the invention. Before treatment with a potential agonist, arrestin coupled to a detectable molecule may be detected evenly distributed in the cell cytoplasm. The detectable molecules emit energy, from which a first image may be generated. The cells are scanned according to the detection method utilized, and an image of the cells is generated. The image of the cells before treatment with an agonist will show the detectable molecules to be fairly evenly distributed in the cell cytoplasm.

The intensity of energy emitted from the detectable molecules may be measured, converted to a digital format, and represented as pixels. For example, the image may be mapped according to the position and intensity of each pixel. The pixels at a given intensity may be quantified and a mean intensity for the pixels may be calculated. The digitized image may be redisplayed on a video display.

After treatment with a test compound, the cells are again scanned according to the detection method utilized, and a second image of the cells is generated. The second image of the cells can be converted to a digital image and analyzed as before.

It may be advantageous to reduce the sensitivity of the detector to prevent saturation of the detector by the intense energy emitted from detectable molecules localized in endocytic vesicles. As can be appreciated, the sensitivity of the detector can be reduced in a number of ways, such as by using energy inhibiting filters at the detector or reducing the gain associated with the detector.

If the test compound is an agonist, then the detectable molecules may be concentrated in specific, smaller areas instead of evenly distributed over the whole area of the cell cytoplasm. If the test compound is not an agonist, then the distribution of detectable molecules would be substantially unchanged.

For example, after treating the cells with an agonist, arrestin may be detected in proximity to GPCRs at a cell membrane and/or colocalized with a GPCR in endocytic vesicles. Since the detectable molecules are concentrated in smaller areas, the energy from the detectable molecules will be concentrated and of a significantly increased intensity. The apparent increase in intensity is due to a redistribution of the detectable molecules into smaller areas, and is not due to an inherent change in the intensity of the energy produced by each detectable molecule.

The energy from detectable molecules concentrated in vesicles may be used to readily indicate activation of the GPCR pathway; therefore, positive and ready identification of these concentrations of detectable molecules is desirable. As explained above, the detectable molecules evenly distributed in the cell cytoplasm give uniform, dilute energy emissions. In comparison, the detectable molecules concentrated in endocytic vesicles give more intense energy emissions.

Figure 2:
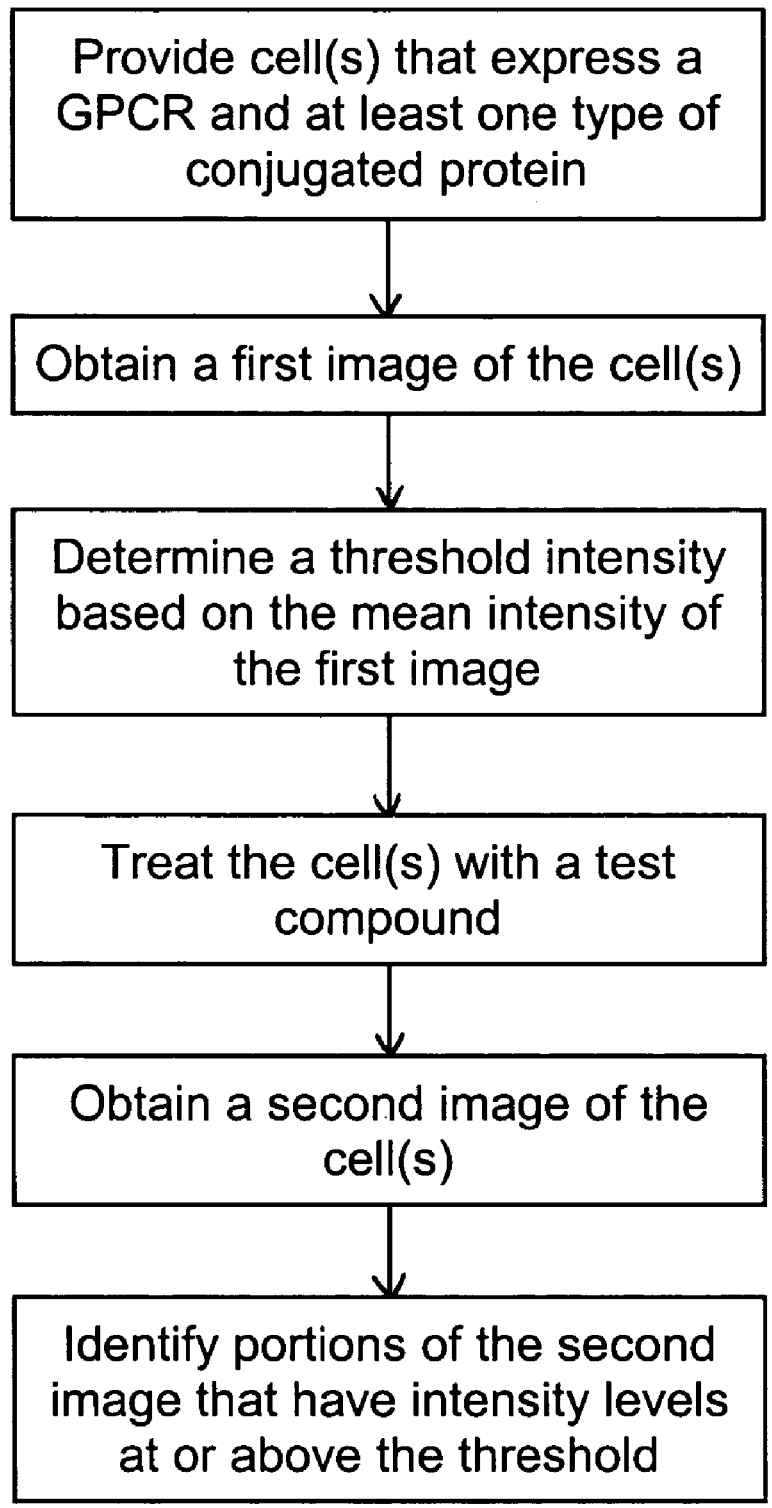
FIG. 2 is a flow diagram of another method of detecting receptor activity in accordance with the invention.

FIG. 2 is a flow diagram of a method of detecting receptor activity in accordance with another aspect of the invention. Based on the energy emissions obtained from detectable molecules evenly distributed in the cell cytoplasm, a mean intensity can be obtained, and from this mean intensity, a threshold intensity can be set. The threshold intensity can be set such that it excludes energy emissions from detectable molecules evenly distributed in the cell cytoplasm (i.e., background emissions), but not energy emissions from detectable molecules colocalized in, for example, endocytic vesicles (i.e., target emissions). The threshold intensity may be, for example, the mean intensity of all energy emissions in a control cell (i.e., a cell not treated with an agonist) plus a determined number of standard deviations, such as two standard deviations (95th percentile) or three standard deviations (>99th percentile). The method of determining the threshold intensity is not controlling as long as the threshold is set to exclude as much of the background emissions as possible while permitting the detection of as much of the target emissions as possible.

It should be emphasized that the first image may be taken of a control group of cells rather than the group of cells that are treated with the test compound. For example, once it is determined how much conjugated protein a particular cell line expresses, this information can be used to determine the mean intensity for the cell line. The mean intensity for the cell line can be used to set the threshold intensity in subsequent experiments.

After a threshold intensity is set, the energy emissions above the threshold intensity can be identified and quantified. The identified energy emissions may be tagged using a computer memory or the identified energy emissions may be marked in a computer generated image by changing the associated pixels to a unique color, for example, magenta. The computer generated image may be redisplayed on a video display after identifying (for example, by magenta) the portions of the image which have energy emissions at or above the threshold intensity.

The pixels corresponding to energy emissions at or above the threshold intensity may be quantified by absolute number (i.e. they may be counted), as a percentage of the total number of pixels, or, preferably, as a weighted sum of pixels above the threshold intensity. The weights may be assigned in a variety of ways. For example, each pixel above the threshold intensity may be weighted according to its respective intensity value. The number of energy emissions above the threshold intensity may be used to determine whether and to what degree GPCRs have been activated. For example, a large number of energy emissions above the threshold may indicate activation. The number of energy emissions above the threshold intensity may also be used to determine whether and to what degree GPCRs have been deactivated. For example, very few energy emissions above the threshold may indicate deactivation.

The number of energy emissions above the threshold intensity may be used to indicate activation in a variety of ways. For example, to indicate activation, a number or a percentage of energy emissions above the threshold may be set. If this set number or percentage is exceeded, it may be determined that the GPCR pathway has been activated. Further, the number of energy emissions above the threshold in the control (i.e., untreated) cells and treated cells may be compared and a number by which the treated cells' emissions exceed the control cells' emissions may be set. If this set number is exceeded, it may be determined that the GPCR pathway has been activated.

By way of example, in the automated methods of the present invention one or more cells that express a GPCR and that contain a conjugate of an arrestin protein and a detectable molecule are provided. The cells are scanned according to the method of detection to generate an image of the cells based on the relative intensity of energy emissions from the detectable molecules. The image may be digitized and the relative intensity of energy emissions may be converted to pixel intensity values. Using the intensity of the energy emissions, activation or deactivation of the GPCR pathway may be detected. For example, a considerable amount of energy above a calculated threshold intensity may indicate activation of the GPCR pathway. Likewise, a significant decrease in the amount of energy above a calculated threshold intensity may indicate deactivation of the GPCR pathway.

For example, a mean intensity of the first image can be calculated, either directly from the first image or by analyzing the first array of pixels. A threshold intensity may be set to exclude energy emissions from detectable molecules evenly distributed in the cell cytoplasm but not energy emissions from detectable molecules in endocytic vesicles, for example, at two or three standard deviations above the mean intensity of the energy emissions in the first image (before exposure to the test compound or solution). The energy emissions above this threshold intensity may be identified and quantified. To identify the energy emissions, the associated pixels may be tagged using a computer memory or the pixels may be changed in a computer generated image to a unique color, for example, magenta. The image may be redisplayed on a video display after identifying (for example, by magenta) those pixels which are above the threshold intensity. The pixels above the threshold intensity may be quantified as a weighted sum.

A comparison of the number of pixels above the threshold before and after exposure to the test compound or solution may be used to determine if the test compound or solution is or contains an agonist. If, for example, the test compound or solution is or contains an agonist, the number of pixels above the threshold after exposure to the agonist may dramatically increase.

The automated methods of the present invention may also be used to screen test compounds and test solutions for GPCR antagonist activity. One or more cells that express a GPCR and that contain a conjugate of an arrestin protein and a detectable molecule are provided. The cells are scanned according to the method of detection to generate a first image of the cells.

The cells are exposed to a test compound or test solution and then to a known agonist. The cells are scanned again according to the method of detection to generate a second image of the cells. The first and second images may be captured as or converted to first and second sets of pixels. The intensity of the first and second sets of pixels may be measured. As discussed above, the intensity of the first and second sets of pixels can be used to determine whether the GPCR pathway has been activated. For example, if the test compound is an antagonist, activation of the GPCR pathway would be blocked.

A comparison of the number of signals above the threshold before and after exposure to the test compound or solution and the agonist may be used to determine if the test compound or solution is or contains an antagonist. If, for example, the test compound or solution is or contains an antagonist, then the number of energy emissions above the threshold before and after exposure to the agonist and test compound or solution may remain fairly constant instead of increasing as expected due to the agonist.

The invention will be further explained by the following illustrative example, which is intended to be non-limiting.

EXAMPLE

Determination of Agonist Mediated Translocation of βarr-GFP

Agonist mediated translocation of the βarr-GFP chimera from cell cytosol to endocytic vesicles was studied using a double stable cell line (stable for the βarr-GFP and the V2R), for example, HEK-293 cells or COS cells. These cells were transfected with plasmids containing cDNA for the V2R receptor and for the βarr-GFP conjugate.

Cells were assessed using confocal microscopy to detect the fluorescence of GFP (FIGS. 3a and 3b). Images were collected sequentially using single line excitation (488 nm) with a Zeiss laser scanning confocal microscope (LSM-510).

In the absence of agonist, βarr-GFP was detected evenly distributed throughout the cytoplasm of cells expressing the V2R as indicated by the homogeneous βarr-GFP fluorescence in FIG. 3a. Addition of arginine vasopressin (AVP, obtained from Sigma Chemicals, St. Louis, Mo.) promoted rapid redistribution of βarr-GFP from the cytoplasm to the receptor at the plasma membrane. A more prolonged exposure to the agonist (i.e., after 30 min.), βarr-GFP redistributed to endocytic vesicles (FIG. 3b).

The upper confocal microscopy images of FIGS. 3a and 3b were taken at standard sensitivity and the intense energy emitted from detectable molecules localized in endocytic vesicles saturated the detector (i.e., when attempting to plot the intensities of the emissions captured as pixels, the intensities were off the scale). FIGS. 4a and 4b are identical to FIGS. 3a and 3b, respectively, except that they were taken at a reduced sensitivity to prevent saturation of the detector by βarr-GFP colocalized in endocytic vesicles. FIGS. 4a and 4b demonstrate that concentration of βarr-GFP in endocytic vesicles produces spots of fluorescent intensity much greater than the fluorescent intensity observed in the cytoplasm of the control cells.

Using the non-saturated images (those in FIGS. 4a and 4b), the energy emissions were captured as pixels. The computer program IP Labs for Windows Version 3.0.6 (Scanalytics, Inc., Fairfax, Va.) was used to analyze the data. The position and intensity of the pixels were mapped, generating a matrix. A histogram of pixel count versus pixel intensity was generated using the control cells. The mean intensity of the pixels in the control cells was calculated and a standard deviation was calculated.

Figure 5A:
Figure 5B:

The threshold intensity was calculated as the mean cell intensity plus three standard deviations (>99th percentile). Pixels with intensities above the threshold were indicated in a magenta color in both the control and treated images (FIGS. 5A and 5b, respectively). The control cells had very few magenta-colored pixels. In contrast, the cells treated with agonist (the treated cells) had many magenta-colored pixels. The magenta-colored pixels in the treated cells of FIG. 5b closely correspond to the βarr-GFP containing endocytic vesicles in FIG. 4b.

Figures 6, 7:
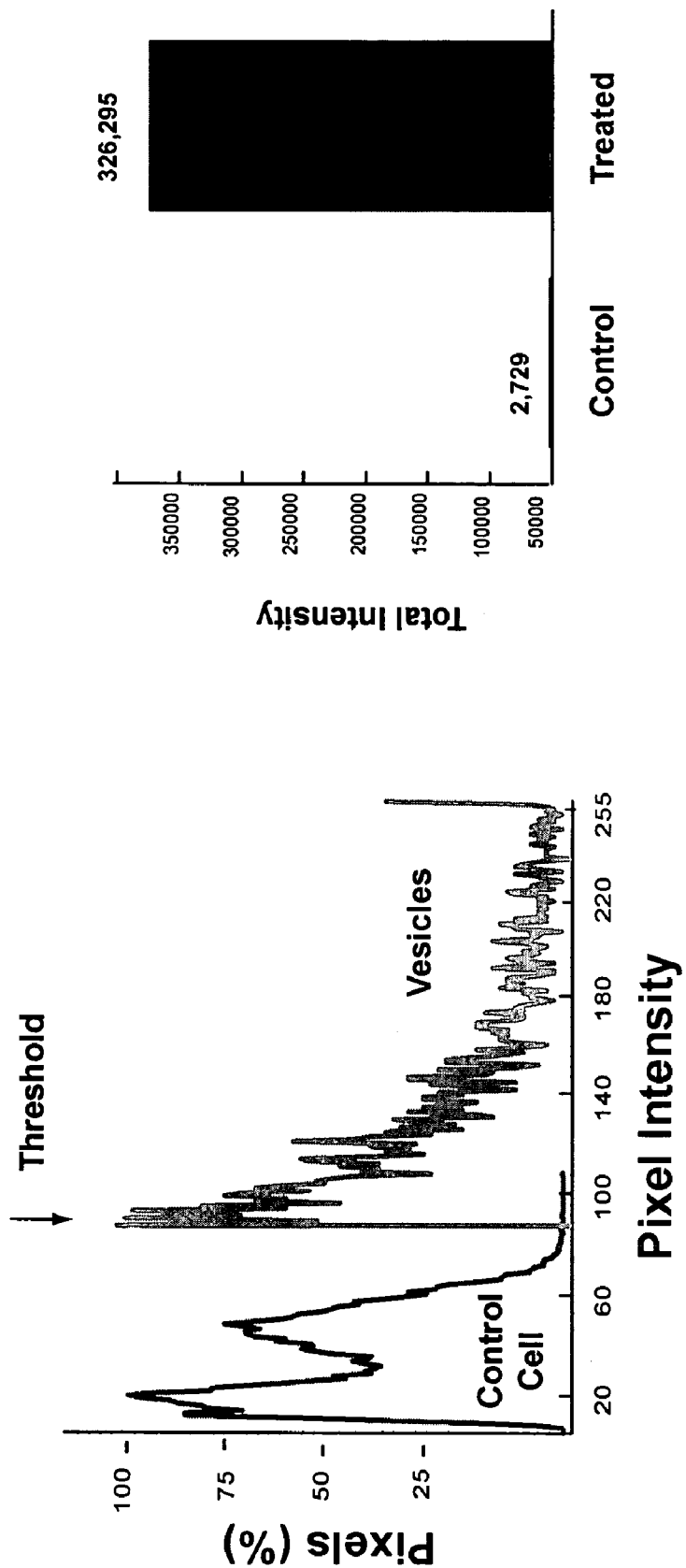
FIG. 6 is a histogram of pixel count vs pixel intensity.
FIG. 7 is a graph of the number of pixels above the threshold intensity for the control and treated cells.

The pixels above the threshold in both the control cells and treated cells were tabulated. FIG. 6 graphs the pixels in both the control cells and treated cells that are above the threshold. The first curve, labeled Control Cell, is a histogram of pixel count versus pixel intensity generated using the control cells. The second curve, labeled Vesicles, indicates pixels above the threshold in both the treated and control cells, and thus corresponds to vesicles in the treated cells. The threshold was set at the mean cell intensity of the control cells plus three standard deviations (>99th percentile).

FIG. 7 is a graph of the number of pixels above the threshold intensity for the control and treated cells. The number of pixels above the threshold in the treated cells is approximately 120 times that of the control cells. This data readily may be used to indicate that an agonist was added and the βarr-GFP translocated to endocytic vesicles.

Various modifications and alterations of this invention will become apparent to those skilled in the art without departing from the scope and spirit of this invention. These and other alternate embodiments are intended to fall within the scope of the claims which follow.

TABLE 1

Human G Protein Coupled Receptor Family
(Receptors known as of January, 1999)

| CLASS | LIGAND | NUMBER | TISSUE | PHYSIOLOGY | THERAPEUTICS |
|---|---|---|---|---|---|
| Class I | Amine | | | | |
| Rhodopsin like | Acetylcholine (muscarinic & nicotinic) Adrenoceptors | 5 | Brain, Nerves, Heart | Neurotransmitter | Acuity, Alzheimer's |
| | Alpha Adrenoceptors | 6 | Brain, Kidney, Lung | Gluconeogenesis | Diabetes, Cardiovascular |
| | Beta Adrenoceptors | 3 | Kidney, Heart | Muscle Contraction | Cardiovascular, Respiratory |
| | Dopamine | 5 | Brain, Kidney, GI | Neurotransmitter | Cardiovascular, Parkinson's |

TABLE 1-continued

Human G Protein Coupled Receptor Family
(Receptors known as of January, 1999)

| CLASS | LIGAND | NUMBER | TISSUE | PHYSIOLOGY | THERAPEUTICS |
|---|---|---|---|---|---|
| | Histamine | 2 | Vascular, Heart, Brain | Vascular Permeability | Anti-inflammatory, Ulcers |
| | Serotonin (5-HT) | 16 | Most Tissues | Neurotransmitter | Depression, Insomnia, Analgesic |
| | Peptide | | | | |
| | Angiotensin | 2 | Vascular, Liver, Kidney | Vasoconstriction | Cardiovascular, Endocrine |
| | Bradykinin | 1 | Liver, Blood | Vasodilation, | Anti-inflammatory, Asthma |
| | C5a anaphylatoxin | 1 | Blood | Immune System | Anti-inflammatory |
| | Fmet-leu-phe | 3 | Blood | Chemoattractant | Anti-inflammatory |
| | Interleukin-8 | 1 | Blood | Chemoattractant | Anti-inflammatory |
| | Chemokine | 6 | Blood | Chemoattractant | Anti-inflammatory |
| | Orexin | 2 | Brain | Fat Metabolism | Obesity |
| | Nociceptin | 1 | Brain | Bronchodilator, Pain | Airway Diseases, Anesthetic |
| | CCK (Gastrin) | 2 | Gastrointestinal | Motility, Fat Absorption | Gastrointestinal, Obesity, Parkinson's |
| | Endothelin | 2 | Heart, Bronchus, Brain | Muscle Contraction | Cardiovascular, Respiratory |
| | Melanocortin | 5 | Kidney, Brain | Metabolic Regulation | Anti-inflammatory, Analgesics |
| | Neuropeptide Y | 5 | Nerves, Intestine, Blood | Neurotransmitter | Behavior, Memory, Cardiovascular |
| | Neurotensin | 1 | Brain, | CNS | Cardiovascular, Analgesic |
| | Opioid | 3 | Brain, | CNS | Depression, Analgesic |
| | Somatostatin | 5 | Brain, Gastrointestinal | Neurotransmitter | Oncology, Alzheimer's |
| | Tachykinin (Substance P, $NKA_1$) | 3 | Brain Nerves | Neurohormone | Depression, Analgesic |
| | Thrombin | 3 | Platelets, Blood Vessels | Coagulation | Anti-coagulant, Anti-inflammatory |
| | Vasopressin-like | 4 | Arteries, Heart, Bladder | Water Balance | Anti-diuretic, Diabetic Complications |
| | Galanin | 1 | Brain, Pancreas | Neurotransmitter | Analgesics, Alzheimer's |
| | Hormone protein | | | | |
| | Follicle stimulating hormone | 1 | Ovary, Testis | Endocrine | Infertility |
| | Lutropin-choriogonadotropic | 1 | Ovary, Testis | Endocrine | Infertility |
| | Thyrotropin | 1 | Thyroid | Endocrine | Thyroidism, Metabolism |
| | (Rhod)opsin | | | | |
| | Opsin | 5 | Eye | Photoreception | Ophthalmic Diseases |
| | Olfactory | 4(~1000) | Nose | Smell | Olfactory Diseases |
| | Prostanoid | | | | |
| | Prostaglandin | 5 | Arterial, Gastrointestinal | Vasodilation, Pain | Cardiovascular, Analgesic |
| | Lysophosphatidic Acid | 2 | Vessels, Heart, Lung | Inflammation | Cancer, Anti-Inflammatory |
| | Sphingosine-1-phosphate | 2 | Most Cells | Cell proliferation | Cancer |
| | Leukotriene | 1 | White Blood Cells, Bronchus | Inflammation | Asthma, Rheumatoid Arthritis |
| | Prostacyclin | 1 | Arterial, Gastrointestinal | Platelet Regulation | Cardiovascular |
| | Thromboxane | 1 | Arterial, Bronchus | Vasoconstriction | Cardiovascular, Respiratory |
| | Nucleotide-like | | | | |
| | Adenosine | 4 | Vascular, Bronchus | Multiple Effects | Cardiovascular, Respiratory |
| | Purinoceptors | 4 | Vascular, Platelets | Relaxes Muscle | Cardiovascular, Respiratory |
| | Cannabis | 2 | Brain | Sensory Perception | Analgesics, Memory |
| | Platelet activating factor | 1 | Most Peripheral Tissues | Inflammation | Anti-inflammatory, Anti-asthmatic |
| | Gonadotropin-releasing hormone like | | | | |
| | Gonadotropin-releasing hormone | 1 | Reproductive Organs, Pituitary | Reproduction | Prostate Cancer, Endometriosis |
| | Thyrotropin-releasing hormone | 1 | Pituitary, Brain | Thyroid Regulation | Metabolic Regulation |
| | Growth hormone-inhibiting factor | 1 | Gastrointestinal | Neuroendocrine | Oncology, Alzheimer's |
| | Melatonin | 1 | Brain, Eye, Pituitary | Neuroendocrine | Regulation of Circadian Cycle |
| Class II Secretin like | Secretin | 1 | Gastrointestinal, Heart | Digestion | Obesity, Gastrointestinal |
| | Calcitonin | 1 | Bone, Brain | Calcium Resorption | Osteoporosis |
| | Corticotropin releasing factor/urocortin | 1 | Adrenal, Vascular, Brain | Neuroendocrine | Stress, Mood, Obesity |
| | Gastric inhibitory peptide (GIP) | 1 | Adrenals, Fat Cells | Sugar/Fat Metabolism | Diabetes, Obesity |
| | Glucagon | 1 | Liver, Fat Cells, Heart | Gluconeogenesis | Cardiovascular |
| | Glucagon-like Peptide 1 (GLP-1) | 1 | Pancreas, Stomach, Lung | Gluconeogenesis | Cardiovascular, Diabetes, Obesity |

TABLE 1-continued

Human G Protein Coupled Receptor Family
(Receptors known as of January, 1999)

| CLASS | LIGAND | NUMBER | TISSUE | PHYSIOLOGY | THERAPEUTICS |
|---|---|---|---|---|---|
| | Growth hormone-releasing hormone | 1 | Brain | Neuroendocrine | Growth Regulation |
| | Parathyroid hormone | 1 | Bone, Kidney | Calcium Regulation | Osteoporosis |
| | PACAP | 1 | Brain, Pancreas, Adrenals | Metabolism | Metabolic Regulation |
| | Vasoactive intestinal polypeptide (VIP) | 1 | Gastrointestinal | Motility | Gastrointestinal |
| Class III | Metabotropic Glutamate | 7 | Brain | Sensory Perception | Hearing, Vision |
| | $GABA_B$ | 1 | Brain | Neurotransmitter | Mood Disorders |
| | Extracellular Calcium Sensing | 1 | Parathyroid, Kidney, GI Tract | Calcium Regulation | Cataracts, GI Tumors |

Figure 2

G protein-coupled receptors:

(Division into Class A or Class B)

1. A1 adenosine receptor [Homo sapiens]. ACCESSION AAB25533 npivyaf riqkfrvtfl kiwndhfrcq pappidedlp eerpdd

Class A

2. adrenergic, alpha -1B-, receptor [Homo sapiens]. ACCESSION NP_000670 npiiypcsskefkrafvrilgcqcrgrgrrrrrrrrrlggcaytyrpwtrggslersqsrkdslddsgsclsgsqrtlpsaspspgylgrga pppvelcafpewkapgallslpapeppgrrgrhdsgplftfklltepespgtdggasnggceaaadvangqpgfksnmplapg qf Class A 3. adrenergic receptor alpha-2A [Homo sapiens]. ACCESSION AAG00447 npviytifnhdfrrafkkilcrgdrkriv

Class A

4. alpha-2B-adrenergic receptor - human. ACCESSION A37223 npviytifnqdfrrafrrilcrpwtqtaw

Class A

5. alpha-2C-adrenergic receptor - human. ACCESSION A31237 npviytvfnqdfrpsfkhilfrrrrrgfrq

Class A

6. beta-1-adrenergic receptor [Homo sapiens]. ACCESSION NP_000675 npiiycrspdfrkafqgllccarraarrrhathgdrprasgclarpgpppspgaasdddddddvvgatpparllepwagcnggaaa dsd ssldepcrpgfaseskv Class A 7. beta-2 adrenergic receptor. ACCESSION P07550 npliycrspdfriafqellclrrsslkaygngyssngntgeqsgyhveqekenkllcedlpgtedfvghqgtvpsdnidsqgmcstndsll Class A 8. dopamine receptor D1 [Homo sapiens]. ACCESSION NP_000785 npiiyafnadfrkafstllgcyrlcpatnnaietvsinnngaamfsshheprgsiskecnlvyliphavgssedlkkeeaagiarpleklspalsvildydtdvslekiqpitqngqhpt Class A 9. D(2) dopamine receptor. ACCESSION P14416 npiiyttfniefrkaflkilhc

Class A

10. d3 dopamine receptor - human. ACCESSION G01977 npviyttfniefrkaflkilsc

Class A

11. dopamine receptor D4 - human. ACCESSION DYHUD4 npviytvfnaefrnvfrkalracc

Class A

12. dopamine receptor D5 - human. ACCESSION DYHUD5 npviyafnadfqkvfaqllgcshfcsrtpvetvnisnelisynqdivfhkeiaaayihmmpnavtpgnrevdndeeegpfdrmfqiyqtspdgdpvaesvweldcegeisldkitpftpngfh Class A 13. muscarinic acetylcholine receptor M1 [Homo sapiens]. ACCESSION NP_000729 npmcyalcnkafrdtfrllllcrwdkrrwrkipkrpgsvhrtpsrqc

Class A 14. muscarinic acetylcholine receptor M2 [Homo sapiens]. ACCESSION NP_000730 npacyalcnatfkktfkhllmchyknigatr

Class A 15. muscarinic acetylcholine receptor M3 [Homo sapiens].

npvcyalcnktfrttfkmlllcqcdkkkrrkqqyqqrqsvifhkrapeqal

Class A 16. muscarinic acetylcholine receptor M4 [Homo sapiens]. ACCESSION NP_000732 npacyalcnatfkktfrhlllcqymigtar

Class A 17. m5 muscarinic receptor. locus HUMACHRM ACCESSION AAA51569 npicyalcnrtfrktfkmlllcrwkkkkveeklywqgnsklp

Class A 18. 5-hydroxytryptamine (serotonin) receptor 1A [Homo sapiens]. ACCESSION BAA90449 npviyayfnkdfqnafkkiikckf

Class A 19. 5-hydroxytryptamine (serotonin) receptor 1B [Homo sapiens]. ACCESSION BAA94455 npiiytmsnedfkqafhklirfkcts

Class A 20. 5-hydroxytryptamine (serotonin) receptor 1E [Homo sapiens]. ACCESSION BAA94458 npllytsfnedfklafkklircre

Class A

21. OLFACTORY RECEPTOR 6A1. ACCESSION O95222 npiiyclmqevkralccilhlyqhqdpdpkkgsmv

Class A

22. OLFACTORY RECEPTOR 2C1. ACCESSION O95371 npliytlmmevkgalrrllgkgrevg

Class A

23. angiotensin receptor 1 [Homo sapiens]. ACCESSION NP_033611 nplfygflgkkfkryflqllkyippkakshsnlsfkmsfisyrpsdnvssstkkpapcfeve

Class B

24. angiotensin receptor 2 [Homo sapiens]. ACCESSION NP_000677 npflycfvgnrfqqklrsvfrvpitwlqgkresmscrkssslremetfvs

Class B

25. interleukin 8 receptor beta (CXCR2) [Homo sapiens]. ACCESSION NM_001557

NPLIYAFIGQKFRHGLLKILAIHGLISKDSLPKDSRPSFVGSSSGHTSTTL

Class B

26. cx3c chemokine receptor 1 (cx3cr1) (fractalkine receptor)
ACCESSION P49238 npliyafagekfrrylyhlygkclavlcgrsvhvdfsssesqrsrhgsvlssnftyhtsdgdallll

Class B

27. neurotensin receptor - human. ACCESSION S29506 n pilynlvsanfrhiflatlaclcpvwrrrrkrpafsrkadsvssnhflssnatretly

Class B

28. SUBSTANCE-P RECEPTOR (SPR) (NK-1 RECEPTOR) (NK-1R). ACCESSION P25103 npiiyccIndrfrlgfkhafrccpfisagdyeglemkstrylqtqgsvykvsrletfistvvgaheeepedgpkafpssldltsncssr
sdsktmtesfsfssnvls

Class B

29. vasopressin receptor type 2 [Homo sapiens]. ACCESSION AAD16444 npwiyasfsssvsselrsllccargrtppslgpqde*scttassss*lakd*tss*

Class B

30. thyrotropin-releasing hormone receptor - human. ACCESSION JN0708 npviynlmsqkfraafrklcnckqkptekpanysvalnysvikesdhf*s*f*eldditv*f*dt*yl*saf*kvsfddtclasevsfsqs Class B 31. oxytocin receptor - human. ACCESSION A55493 npwiymlftghlfhelvqrflccsasylkgrrlgetsaskksns*sssfvlshrsssqrscsqpsta*

Class B

32. neuromedin U receptor 1 [Homo sapiens]. ACCESSION AAG24793 npvlyslmssrfretfqealclgacchrlrprhsshslsrmttgstlcdvgslgswvhplagndgpeaqqetdps

Class B

33. gastrin receptor. ACCESSION AAC37528 nplvycfmhrrfrqacletcarccprpprarpralpdedpptpsiaslsrlsyttistlgpg

Class B

34. galanin receptor 3 [Homo sapiens]. ACCESSION 10879541 nplvyalasrhfrarfrrlwpcgrrrrhrarralrrvrpassgppgcpgdarpsgrllagggqgpepregpvhggeaargpe Class A 35. edg-1 - human. ACCESSION A35300 npiiytltnkemrrafirimscckcpsgdsagkfkrpiiagmefsrsksdnsshpqkdegdnpetimssgnvnsss

Class A

36. central cannabinoid receptor [Homo sapiens]. ACCESSION NP_057167 npiiyalrskdlrhafrsmfpscegtaqpldnsmgdsdclhkhannaasvhraaescikstvkiakvtmsvstdtsaeal Class A 37. delta opioid receptor - human. ACCESSION I38532 npvlyafldenfkrcfrqlcrkpcgrpdpssfsrpreatarervtactpsdgpgggraa

Class A

38. proteinase activated receptor 2 (PAR-2) human. ACCESSION P55085 dpfvyyfvshdfrdhaknallcrsvrtvkqmqvsltskkhsrksssysssttvktsy

Class B

39. vasopressive intestinal peptide receptor (VIPR) rat. ACCESSION NM_012685

NGEVQAELRRKWRRWHLQGVLGWSSKSQHPWGGSNGATCSTQVSMLTRVSPSARR
   SSSFQAEVSLV

Class B

What is claimed is:

1. A method of detecting G protein-coupled receptor (GPCR) pathway activity, comprising:

providing at least one cell that expresses a GPCR and a plurality of conjugated proteins, each of the plurality of conjugated proteins formed by conjugating an arrestin protein and a detectable molecule, the plurality of conjugated proteins being distributed evenly in the cytoplasm of the at least one cell;

obtaining a first image of the at least one cell by detecting an amount of energy emitted from the detectable molecules and storing a value relative to the amount of energy;

providing a threshold intensity such that the energy emitted from detectable molecules distributed evenly in the cytoplasm are excluded;

treating the at least one cell with a test compound;

obtaining a second image of the at least one cell by detecting an amount of energy emitted from the detectable molecules and storing a value relative to the amount of energy; and comparing the first image and the second image to detect the localization of at least some of the plurality of conjugated proteins at at least one of endocytic vesicles and endosomes, wherein a difference between the value relative to the amount of energy of the detectable molecules of the first image and the value relative to the amount of energy of the detectable molecules of the second image detects the localization, thereby detecting GPCR pathway activity.

2. The method of claim 1, wherein the threshold intensity is set to exclude the energy emitted from the detectable molecules that are evenly distributed in the cytoplasm and include the energy emitted from the detectable molecules in endocytic vesicles.

3. The method of claim 1, wherein the threshold intensity is set at the mean intensity of all energy emitted in a control cell plus two standard deviations.

4. The method of claim 1, wherein the threshold intensity is set at the mean intensity of all energy emitted in a control cell plus three standard deviations.

5. The method of claim 1, wherein the test compound is a potential agonist or a potential antagonist.

6. A method of detecting G protein-coupled receptor (GPCR) pathway activity, comprising:

providing at least one cell that expresses a GPCR and a plurality of conjugated proteins, each of the plurality of conjugated proteins formed by conjugating an arrestin protein and a detectable molecule, the plurality of conjugated proteins being distributed in the cytoplasm of the at least one cell;

obtaining a first digital image of the at least one cell by detecting and measuring energy emitted from the detectable molecules, the first digital image being formed from an array of a plurality of pixels each having respective intensity values, a respective intensity value being based on the intensity of energy emitted from the detectable molecules associated with a pixel's location in the array;

providing a threshold intensity such that the energy emitted from detectable molecules distributed evenly in the cytoplasm are excluded;

treating the at least one cell with a test compound;

obtaining a second digital image of the at least one cell by detecting and measuring energy emitted from the detectable molecules, the second digital image being formed from an array of a plurality of pixels each having respective intensity values, a respective intensity value being based on the intensity of energy emitted from the detectable molecules associated with a pixel's location in the array; and comparing the first digital image and the second digital image to detect the localization of at least some of the plurality of conjugated proteins at at least one of endocytic vesicles and endosomes wherein, the localization of at least some of the plurality of conjugated proteins is detected by a change between the first digital image and the second digital image in apparent intensity of energy emitted from detectable molecules resulting in an increase in the value of at least some of the plurality of pixels thereby detecting GPCR pathway activity.

* * * * *

SEQUENCE LISTING

<160> NUMBER OF SEQ ID NOS: 40

<210> SEQ ID NO 1
<211> LENGTH: 43
<212> TYPE: PRT
<213> ORGANISM: Human

<400> SEQUENCE: 1

Asn Pro Ile Val Tyr Ala Phe Arg Ile Gln Lys Phe Arg Val Thr Phe
1               5                   10                  15

Leu Lys Ile Trp Asn Asp His Phe Arg Cys Gln Pro Ala Pro Pro Ile
                20                  25                  30

Asp Glu Asp Ile Pro Glu Glu Arg Pro Asp Asp
            35                  40

<210> SEQ ID NO 2
<211> LENGTH: 177
<212> TYPE: PRT
<213> ORGANISM: Human

<400> SEQUENCE: 2

Asn Pro Ile Ile Tyr Pro Cys Ser Ser Lys Glu Phe Lys Arg Ala Phe
1               5                   10                  15

Val Arg Ile Leu Gly Cys Gln Cys Arg Gly Arg Gly Arg Arg Arg Arg
                20                  25                  30

Arg Arg Arg Arg Arg Ile Gly Gly Cys Ala Tyr Thr Tyr Arg Pro Trp
            35                  40                  45

Thr Arg Gly Gly Ser Leu Glu Arg Ser Gln Ser Arg Lys Asp Ser Leu
        50                  55                  60

Asp Asp Ser Gly Ser Cys Ile Ser Gly Ser Gln Arg Thr Leu Pro Ser
65                  70                  75                  80

Ala Ser Pro Ser Pro Gly Tyr Leu Gly Arg Gly Ala Pro Pro Pro Val
                85                  90                  95

Glu Leu Cys Ala Phe Pro Glu Trp Lys Ala Pro Gly Ala Leu Leu Ser
            100                 105                 110

Leu Pro Ala Pro Glu Pro Pro Gly Arg Arg Gly Arg His Asp Ser Gly
        115                 120                 125

Pro Leu Phe Thr Phe Lys Leu Leu Thr Glu Pro Glu Ser Pro Gly Thr
130                 135                 140

Asp Gly Gly Ala Ser Asn Gly Gly Cys Glu Ala Ala Ala Asp Val Ala
145                 150                 155                 160

Asn Gly Gln Pro Gly Phe Lys Ser Asn Met Pro Leu Ala Pro Gly Gln
                165                 170                 175

Phe

<210> SEQ ID NO 3
<211> LENGTH: 29
<212> TYPE: PRT
<213> ORGANISM: Human

<400> SEQUENCE: 3

Asn Pro Val Ile Tyr Thr Ile Phe Asn His Asp Phe Arg Arg Ala Phe
1               5                   10                  15

Lys Lys Ile Leu Cys Arg Gly Asp Arg Lys Arg Ile Val
                20                  25

<210> SEQ ID NO 4
<211> LENGTH: 29
<212> TYPE: PRT
<213> ORGANISM: Human

<400> SEQUENCE: 4

Asn Pro Val Ile Tyr Thr Ile Phe Asn Gln Asp Phe Arg Arg Ala Phe
1               5                   10                  15

Arg Arg Ile Leu Cys Arg Pro Trp Thr Gln Thr Ala Trp
            20                  25

<210> SEQ ID NO 5
<211> LENGTH: 30
<212> TYPE: PRT
<213> ORGANISM: Human

<400> SEQUENCE: 5

Asn Pro Val Ile Tyr Thr Val Phe Asn Gln Asp Phe Arg Pro Ser Phe
1               5                   10                  15

Lys His Ile Leu Phe Arg Arg Arg Arg Gly Phe Arg Gln
            20                  25                  30

<210> SEQ ID NO 6
<211> LENGTH: 105
<212> TYPE: PRT
<213> ORGANISM: Human

<400> SEQUENCE: 6

Asn Pro Ile Ile Tyr Cys Arg Ser Pro Asp Phe Arg Lys Ala Phe Gln
1               5                   10                  15

Gly Leu Leu Cys Cys Ala Arg Arg Ala Ala Arg Arg Arg His Ala Thr
            20                  25                  30

His Gly Asp Arg Pro Arg Ala Ser Gly Cys Leu Ala Arg Pro Gly Pro
        35                  40                  45

Pro Pro Ser Pro Gly Ala Ala Ser Asp Asp Asp Asp Asp Val Val
    50                  55                  60

Gly Ala Thr Pro Pro Ala Arg Ile Leu Glu Pro Trp Ala Gly Cys Asn
65                  70                  75                  80

Gly Gly Ala Ala Ala Asp Ser Asp Ser Ser Ile Asp Glu Pro Cys Arg
                85                  90                  95

Pro Gly Phe Ala Ser Glu Ser Lys Val
            100                 105

<210> SEQ ID NO 7
<211> LENGTH: 92
<212> TYPE: PRT
<213> ORGANISM: Human

<400> SEQUENCE: 7

Asn Pro Leu Ile Tyr Cys Arg Ser Pro Asp Phe Arg Ile Ala Phe Gln
1               5                   10                  15

Glu Leu Leu Cys Leu Arg Arg Ser Ser Ile Lys Ala Tyr Gly Asn Gly
            20                  25                  30

Tyr Ser Ser Asn Gly Asn Thr Gly Glu Gln Ser Gly Tyr His Val Glu
        35                  40                  45

Gln Glu Lys Glu Asn Lys Leu Leu Cys Glu Asp Ile Pro Gly Thr Glu
    50                  55                  60

Asp Phe Val Gly His Gln Gly Thr Val Pro Ser Asp Asn Ile Asp Ser
65                  70                  75                  80

```
Gln Gly Arg Asn Cys Ser Thr Asn Asp Ser Leu Leu
                85                  90

<210> SEQ ID NO 8
<211> LENGTH: 120
<212> TYPE: PRT
<213> ORGANISM: Human

<400> SEQUENCE: 8

Asn Pro Ile Ile Tyr Ala Phe Asn Ala Asp Phe Arg Lys Ala Phe Ser
1               5                   10                  15

Thr Leu Leu Gly Cys Tyr Arg Leu Cys Pro Ala Thr Asn Asn Ala Ile
            20                  25                  30

Glu Thr Val Ser Ile Asn Asn Gly Ala Ala Met Phe Ser Ser His
        35                  40                  45

His Glu Pro Arg Gly Ser Ile Ser Lys Glu Cys Asn Leu Val Tyr Leu
    50                  55                  60

Ile Pro His Ala Val Gly Ser Ser Glu Asp Leu Lys Lys Glu Glu Ala
65                  70                  75                  80

Ala Gly Ile Ala Arg Pro Leu Glu Lys Leu Ser Pro Ala Leu Ser Val
                85                  90                  95

Ile Leu Asp Tyr Asp Thr Asp Val Ser Leu Glu Lys Ile Gln Pro Ile
            100                 105                 110

Thr Gln Asn Gly Gln His Pro Thr
            115                 120

<210> SEQ ID NO 9
<211> LENGTH: 22
<212> TYPE: PRT
<213> ORGANISM: Human

<400> SEQUENCE: 9

Asn Pro Ile Ile Tyr Thr Phe Phe Asn Ile Glu Phe Arg Lys Ala Phe
1               5                   10                  15

Leu Lys Ile Leu His Cys
            20

<210> SEQ ID NO 10
<211> LENGTH: 22
<212> TYPE: PRT
<213> ORGANISM: Human

<400> SEQUENCE: 10

Asn Pro Val Ile Tyr Thr Phe Phe Asn Ile Glu Phe Arg Lys Ala Phe
1               5                   10                  15

Leu Lys Ile Leu Ser Cys
            20

<210> SEQ ID NO 11
<211> LENGTH: 24
<212> TYPE: PRT
<213> ORGANISM: Human

<400> SEQUENCE: 11

Asn Pro Val Ile Tyr Thr Val Phe Asn Ala Glu Phe Arg Asn Val Phe
1               5                   10                  15

Arg Lys Ala Leu Arg Ala Cys Cys
            20

<210> SEQ ID NO 12
```

```
<211> LENGTH: 123
<212> TYPE: PRT
<213> ORGANISM: Human

<400> SEQUENCE: 12

Asn Pro Val Ile Tyr Ala Phe Asn Ala Asp Phe Gln Lys Val Phe Ala
  1               5                  10                  15

Gln Leu Leu Gly Cys Ser His Phe Cys Ser Arg Thr Pro Val Glu Thr
             20                  25                  30

Val Asn Ile Ser Asn Glu Leu Ile Ser Tyr Asn Gln Asp Ile Val Phe
         35                  40                  45

His Lys Glu Ile Ala Ala Ala Tyr Ile His Met Met Pro Asn Ala Val
     50                  55                  60

Thr Pro Gly Asn Arg Glu Val Asp Asn Asp Glu Glu Gly Pro Phe
 65                  70                  75                  80

Asp Arg Met Phe Gln Ile Tyr Gln Thr Ser Pro Asp Gly Asp Pro Val
                 85                  90                  95

Ala Glu Ser Val Trp Glu Leu Asp Cys Glu Gly Glu Ile Ser Leu Asp
            100                 105                 110

Lys Ile Thr Pro Phe Thr Pro Asn Gly Phe His
            115                 120

<210> SEQ ID NO 13
<211> LENGTH: 47
<212> TYPE: PRT
<213> ORGANISM: Human

<400> SEQUENCE: 13

Asn Pro Met Cys Tyr Ala Leu Cys Asn Lys Ala Phe Arg Asp Thr Phe
  1               5                  10                  15

Arg Leu Leu Leu Leu Cys Arg Trp Asp Lys Arg Arg Trp Arg Lys Ile
             20                  25                  30

Pro Lys Arg Pro Gly Ser Val His Arg Thr Pro Ser Arg Gln Cys
             35                  40                  45

<210> SEQ ID NO 14
<211> LENGTH: 31
<212> TYPE: PRT
<213> ORGANISM: Human

<400> SEQUENCE: 14

Asn Pro Ala Cys Tyr Ala Leu Cys Asn Ala Phe Phe Lys Lys Phe Phe
  1               5                  10                  15

Lys His Leu Leu Met Cys His Tyr Lys Asn Ile Gly Ala Thr Arg
             20                  25                  30

<210> SEQ ID NO 15
<211> LENGTH: 51
<212> TYPE: PRT
<213> ORGANISM: Human

<400> SEQUENCE: 15

Asn Pro Val Cys Tyr Ala Leu Cys Asn Lys Phe Phe Arg Thr Phe Phe
  1               5                  10                  15

Lys Met Ile Leu Leu Cys Gln Cys Asp Lys Lys Arg Arg Lys Gln
             20                  25                  30

Gln Tyr Gln Gln Arg Gln Ser Val Ile Phe His Lys Arg Ala Pro Glu
             35                  40                  45

Gln Ala Leu
```

-continued

<210> SEQ ID NO 16
<211> LENGTH: 31
<212> TYPE: PRT
<213> ORGANISM: Human

<400> SEQUENCE: 16

Asn Pro Ala Cys Tyr Ala Leu Cys Asn Ala Phe Phe Lys Phe Phe
1               5                   10                  15

Arg His Leu Leu Leu Cys Gln Tyr Arg Asn Ile Gly Thr Ala Arg
            20                  25                  30

<210> SEQ ID NO 17
<211> LENGTH: 42
<212> TYPE: PRT
<213> ORGANISM: Human

<400> SEQUENCE: 17

Asn Pro Ile Cys Tyr Ala Leu Cys Asn Arg Thr Phe Arg Lys Phe
1               5                   10                  15

Lys Met Ile Leu Leu Cys Arg Trp Lys Lys Lys Val Glu Glu Lys
            20                  25                  30

Leu Tyr Trp Gln Gly Asn Ser Lys Leu Pro
        35                  40

<210> SEQ ID NO 18
<211> LENGTH: 24
<212> TYPE: PRT
<213> ORGANISM: Human

<400> SEQUENCE: 18

Asn Pro Val Ile Tyr Ala Tyr Phe Asn Lys Asp Phe Gln Asn Ala Phe
1               5                   10                  15

Lys Lys Ile Ile Lys Cys Lys Phe
            20

<210> SEQ ID NO 19
<211> LENGTH: 26
<212> TYPE: PRT
<213> ORGANISM: Human

<400> SEQUENCE: 19

Asn Pro Ile Ile Tyr Thr Met Ser Asn Glu Asp Phe Lys Gln Ala Phe
1               5                   10                  15

His Lys Leu Ile Arg Phe Lys Cys Thr Ser
            20                  25

<210> SEQ ID NO 20
<211> LENGTH: 24
<212> TYPE: PRT
<213> ORGANISM: Human

<400> SEQUENCE: 20

Asn Pro Leu Leu Tyr Thr Ser Phe Asn Glu Asp Phe Lys Leu Ala Phe
1               5                   10                  15

Lys Lys Leu Ile Arg Cys Arg Glu
            20

<210> SEQ ID NO 21
<211> LENGTH: 37
<212> TYPE: PRT

<213> ORGANISM: Human

<400> SEQUENCE: 21

Asn Pro Ile Ile Tyr Cys Leu Arg Asn Gln Glu Val Lys Arg Ala Leu
1               5                   10                  15

Cys Cys Ile Leu His Leu Tyr Gln His Gln Asp Pro Asp Pro Lys Lys
                20                  25                  30

Gly Ser Arg Asn Val
            35

<210> SEQ ID NO 22
<211> LENGTH: 27
<212> TYPE: PRT
<213> ORGANISM: Human

<400> SEQUENCE: 22

Asn Pro Leu Ile Tyr Thr Ile Arg Asn Met Glu Val Lys Gly Ala Leu
1               5                   10                  15

Arg Arg Leu Leu Gly Lys Gly Arg Glu Val Gly
                20                  25

<210> SEQ ID NO 23
<211> LENGTH: 62
<212> TYPE: PRT
<213> ORGANISM: Human

<400> SEQUENCE: 23

Asn Pro Leu Phe Tyr Gly Phe Leu Gly Lys Lys Phe Lys Arg Tyr Phe
1               5                   10                  15

Leu Gln Leu Leu Lys Tyr Ile Pro Pro Lys Ala Lys Ser His Ser Asn
                20                  25                  30

Ile Ser Thr Lys Met Ser Thr Leu Ser Tyr Arg Pro Ser Asp Asn Val
            35                  40                  45

Ser Ser Ser Thr Lys Lys Pro Ala Pro Cys Phe Glu Val Glu
        50                  55                  60

<210> SEQ ID NO 24
<211> LENGTH: 50
<212> TYPE: PRT
<213> ORGANISM: Human

<400> SEQUENCE: 24

Asn Pro Phe Leu Tyr Cys Phe Val Gly Asn Arg Phe Gln Gln Lys Leu
1               5                   10                  15

Arg Ser Val Phe Arg Val Pro Ile Thr Trp Leu Gln Gly Lys Arg Glu
                20                  25                  30

Ser Met Ser Cys Arg Lys Ser Ser Ile Arg Glu Met Glu Thr Phe
            35                  40                  45

Val Ser
    50

<210> SEQ ID NO 25
<211> LENGTH: 51
<212> TYPE: PRT
<213> ORGANISM: Human

<400> SEQUENCE: 25

Asn Pro Leu Ile Tyr Ala Phe Ile Gly Gln Lys Phe Arg His Gly Leu
1               5                   10                  15

Leu Lys Ile Leu Ala Ile His Gly Leu Ile Ser Lys Asp Ser Leu Pro

```
                    20                  25                  30
Lys Asp Ser Arg Pro Ser Phe Val Gly Ser Ser Ser Gly His Thr Ser
                35                  40                  45
Thr Thr Leu
    50

<210> SEQ ID NO 26
<211> LENGTH: 67
<212> TYPE: PRT
<213> ORGANISM: Human

<400> SEQUENCE: 26

Asn Pro Leu Ile Tyr Ala Phe Ala Gly Glu Lys Phe Arg Arg Tyr Leu
1               5                   10                  15

Tyr His Leu Tyr Gly Lys Cys Leu Ala Val Leu Cys Gly Arg Ser Val
                20                  25                  30

His Val Asp Phe Ser Ser Ser Glu Ser Gln Arg Ser Arg His Gly Ser
                35                  40                  45

Val Leu Ser Ser Asn Phe Thr Tyr His Thr Ser Asp Gly Asp Ala Leu
            50                  55                  60

Leu Ile Leu
65

<210> SEQ ID NO 27
<211> LENGTH: 59
<212> TYPE: PRT
<213> ORGANISM: Human

<400> SEQUENCE: 27

Asn Pro Ile Leu Tyr Asn Leu Val Ser Ala Asn Phe Arg His Ile Phe
1               5                   10                  15

Leu Ala Thr Leu Ala Cys Leu Cys Pro Val Trp Arg Arg Arg Arg Lys
                20                  25                  30

Arg Pro Ala Phe Ser Arg Lys Ala Asp Ser Val Ser Ser Asn His Thr
                35                  40                  45

Leu Ser Ser Asn Ala Thr Arg Glu Thr Leu Tyr
            50                  55

<210> SEQ ID NO 28
<211> LENGTH: 107
<212> TYPE: PRT
<213> ORGANISM: Human

<400> SEQUENCE: 28

Asn Pro Ile Ile Tyr Cys Cys Leu Asn Asp Arg Phe Arg Leu Gly Phe
1               5                   10                  15

Lys His Ala Phe Arg Cys Cys Pro Phe Ile Ser Ala Gly Asp Tyr Glu
                20                  25                  30

Gly Leu Glu Met Lys Ser Thr Arg Tyr Leu Gln Thr Gln Gly Ser Val
                35                  40                  45

Tyr Lys Val Ser Arg Leu Glu Thr Thr Ile Ser Thr Val Val Gly Ala
            50                  55                  60

His Glu Glu Glu Pro Glu Asp Gly Pro Lys Ala Thr Pro Ser Ser Ile
65                  70                  75                  80

Asp Ile Thr Ser Asn Cys Ser Ser Arg Ser Asp Ser Lys Thr Met Thr
                85                  90                  95

Glu Ser Phe Ser Phe Ser Ser Asn Val Leu Ser
                100                 105
```

<210> SEQ ID NO 29
<211> LENGTH: 51
<212> TYPE: PRT
<213> ORGANISM: Human

<400> SEQUENCE: 29

Asn Pro Trp Ile Tyr Ala Ser Phe Ser Ser Ser Val Ser Ser Glu Leu
1               5                   10                  15

Arg Ser Leu Leu Cys Cys Ala Arg Gly Arg Thr Pro Ser Ile Gly
            20                  25                  30

Pro Gln Asp Glu Ser Cys Thr Thr Ala Ser Ser Ser Leu Ala Lys Asp
        35                  40                  45

Thr Ser Ser
    50

<210> SEQ ID NO 30
<211> LENGTH: 83
<212> TYPE: PRT
<213> ORGANISM: Human

<400> SEQUENCE: 30

Asn Pro Val Ile Tyr Asn Leu Met Ser Gln Lys Phe Arg Ala Ala Phe
1               5                   10                  15

Arg Lys Leu Cys Asn Cys Lys Gln Lys Pro Thr Glu Lys Pro Ala Asn
            20                  25                  30

Tyr Ser Val Ala Leu Asn Tyr Ser Val Ile Lys Glu Ser Asp His Phe
        35                  40                  45

Ser Thr Glu Leu Asp Asp Ile Thr Val Thr Asp Thr Tyr Leu Ser Ala
    50                  55                  60

Thr Lys Val Ser Phe Asp Asp Thr Cys Leu Ala Ser Glu Val Ser Phe
65                  70                  75                  80

Ser Gln Ser

<210> SEQ ID NO 31
<211> LENGTH: 65
<212> TYPE: PRT
<213> ORGANISM: Human

<400> SEQUENCE: 31

Asn Pro Trp Ile Tyr Met Leu Phe Thr Gly His Leu Phe His Glu Leu
1               5                   10                  15

Val Gln Arg Phe Leu Cys Cys Ser Ala Ser Tyr Leu Lys Gly Arg Arg
            20                  25                  30

Leu Gly Glu Thr Ser Ala Ser Lys Lys Ser Asn Ser Ser Ser Phe Val
        35                  40                  45

Leu Ser His Arg Ser Ser Gln Arg Ser Cys Ser Gln Pro Ser Thr
    50                  55                  60

Ala
65

<210> SEQ ID NO 32
<211> LENGTH: 75
<212> TYPE: PRT
<213> ORGANISM: Human

<400> SEQUENCE: 32

Asn Pro Val Leu Tyr Ser Leu Met Ser Ser Arg Phe Arg Glu Thr Phe
1               5                   10                  15

```
Gln Glu Ala Leu Cys Leu Gly Ala Cys Cys His Arg Leu Arg Pro Arg
            20                  25                  30

His Ser Ser His Ser Leu Ser Arg Met Thr Thr Gly Ser Thr Leu Cys
        35                  40                  45

Asp Val Gly Ser Leu Gly Ser Trp Val His Pro Leu Ala Gly Asn Asp
    50                  55                  60

Gly Pro Glu Ala Gln Glu Thr Asp Pro Ser
65                  70                  75

<210> SEQ ID NO 33
<211> LENGTH: 62
<212> TYPE: PRT
<213> ORGANISM: Human

<400> SEQUENCE: 33

Asn Pro Ile Val Tyr Cys Phe Met His Arg Phe Arg Gln Ala Cys
 1               5                  10                  15

Leu Glu Thr Cys Ala Arg Cys Cys Pro Arg Pro Arg Ala Arg Pro
            20                  25                  30

Arg Ala Leu Pro Asp Glu Asp Pro Pro Thr Pro Ser Ile Ala Ser Leu
            35                  40                  45

Ser Arg Leu Ser Tyr Thr Thr Ile Ser Thr Ile Gly Pro Gly
    50                  55                  60

<210> SEQ ID NO 34
<211> LENGTH: 82
<212> TYPE: PRT
<213> ORGANISM: Human

<400> SEQUENCE: 34

Asn Pro Leu Val Tyr Ala Leu Ala Ser Arg His Phe Arg Ala Arg Phe
 1               5                  10                  15

Arg Arg Leu Trp Pro Cys Gly Arg Arg Arg His Arg Ala Arg Arg
            20                  25                  30

Ala Leu Arg Arg Val Arg Pro Ala Ser Ser Gly Pro Pro Gly Cys Pro
            35                  40                  45

Gly Asp Ala Arg Pro Ser Gly Arg Leu Leu Ala Gly Gly Gln Gly
    50                  55                  60

Pro Glu Pro Arg Glu Gly Pro Val His Gly Gly Glu Ala Ala Arg Gly
65                  70                  75                  80

Pro Glu

<210> SEQ ID NO 35
<211> LENGTH: 76
<212> TYPE: PRT
<213> ORGANISM: Human

<400> SEQUENCE: 35

Asn Pro Ile Ile Tyr Thr Ile Thr Asn Lys Glu Met Arg Arg Ala Phe
 1               5                  10                  15

Ile Arg Ile Met Ser Cys Cys Lys Cys Pro Ser Gly Asp Ser Ala Gly
            20                  25                  30

Lys Phe Lys Arg Pro Ile Ile Ala Gly Met Glu Phe Ser Arg Ser Lys
            35                  40                  45

Ser Asp Asn Ser Ser His Pro Gln Lys Asp Glu Gly Asp Asn Pro Glu
    50                  55                  60

Thr Ile Met Ser Ser Gly Asn Val Asn Ser Ser Ser
```

65                  70                  75

<210> SEQ ID NO 36
<211> LENGTH: 80
<212> TYPE: PRT
<213> ORGANISM: Human

<400> SEQUENCE: 36

Asn Pro Ile Ile Tyr Ala Leu Arg Ser Lys Asp Ile Arg His Ala Phe
1               5                   10                  15

Arg Ser Met Phe Pro Ser Cys Glu Gly Thr Ala Gln Pro Leu Asp Asn
                20                  25                  30

Ser Met Gly Asp Ser Asp Cys Leu His Lys His Ala Asn Asn Ala Ala
            35                  40                  45

Ser Val His Arg Ala Ala Glu Ser Cys Ile Lys Ser Thr Val Lys Ile
        50                  55                  60

Ala Lys Val Thr Met Ser Val Ser Thr Asp Thr Ser Ala Glu Ala Leu
65                  70                  75                  80

<210> SEQ ID NO 37
<211> LENGTH: 59
<212> TYPE: PRT
<213> ORGANISM: Human

<400> SEQUENCE: 37

Asn Pro Val Leu Tyr Ala Phe Ile Asp Glu Asn Phe Lys Arg Cys Phe
1               5                   10                  15

Arg Gln Leu Cys Arg Lys Pro Cys Gly Arg Pro Asp Pro Ser Ser Phe
                20                  25                  30

Ser Arg Pro Arg Glu Ala Thr Ala Arg Glu Arg Val Thr Ala Cys Thr
            35                  40                  45

Pro Ser Asp Gly Pro Gly Gly Gly Arg Ala Ala
        50                  55

<210> SEQ ID NO 38
<211> LENGTH: 58
<212> TYPE: PRT
<213> ORGANISM: Human

<400> SEQUENCE: 38

Asp Pro Phe Val Tyr Tyr Phe Val Ser His Asp Phe Arg Asp His Ala
1               5                   10                  15

Lys Asn Ala Leu Leu Cys Arg Ser Val Arg Thr Val Lys Gln Met Gln
                20                  25                  30

Val Ser Leu Thr Ser Lys Lys His Ser Arg Lys Ser Ser Ser Tyr Ser
            35                  40                  45

Ser Ser Ser Thr Thr Val Lys Thr Ser Tyr
        50                  55

<210> SEQ ID NO 39
<211> LENGTH: 66
<212> TYPE: PRT
<213> ORGANISM: Rat

<400> SEQUENCE: 39

Asn Gly Glu Val Gln Ala Glu Leu Arg Arg Lys Trp Arg Arg Trp His
1               5                   10                  15

Leu Gln Gly Val Leu Gly Trp Ser Ser Lys Ser Gln His Pro Trp Gly
                20                  25                  30

-continued

```
Gly Ser Asn Gly Ala Thr Cys Ser Thr Gln Val Ser Met Leu Thr Arg
         35                  40                  45

Val Ser Pro Ser Ala Arg Arg Ser Ser Ser Phe Gln Ala Glu Val Ser
 50                  55                  60

Leu Val
 65

<210> SEQ ID NO 40
<211> LENGTH: 5
<212> TYPE: PRT
<213> ORGANISM: Human
<220> FEATURE:
<221> NAME/KEY: VARIANT
<222> LOCATION: (3)...(4)
<223> OTHER INFORMATION: Xaa can be any naturally occurring amino acid

<400> SEQUENCE: 40

Asn Pro Xaa Xaa Tyr
 1               5
```